United States Patent
Wang et al.

(10) Patent No.: US 12,303,611 B2
(45) Date of Patent: May 20, 2025

(54) LIQUID DRESSING FOR PROMOTING WOUND HEALING

(71) Applicant: ZIBO LEYOUYOU AGRICULTURAL TECHNOLOGY CO., LTD., Shandong (CN)

(72) Inventors: Liangfang Wang, Shandong (CN); Kui Zhao, Shandong (CN); Haitao Qiao, Shandong (CN); Kai Wang, Shandong (CN)

(73) Assignee: ZIBO LEYOUYOU AGRICULTURAL TECHNOLOGY CO., LTD., Shandong (CN)

( * ) Notice: Subject to any disclaimer, the term of this patent is extended or adjusted under 35 U.S.C. 154(b) by 0 days.

(21) Appl. No.: 18/708,606

(22) PCT Filed: Sep. 20, 2023

(86) PCT No.: PCT/CN2023/120061
§ 371 (c)(1),
(2) Date: May 9, 2024

(87) PCT Pub. No.: WO2024/078282
PCT Pub. Date: Apr. 18, 2024

(65) Prior Publication Data
US 2024/0416001 A1    Dec. 19, 2024

(30) Foreign Application Priority Data
Oct. 10, 2022   (CN) .......................... 202211237037.7

(51) Int. Cl.
*A61L 26/00* (2006.01)

(52) U.S. Cl.
CPC ....... *A61L 26/0004* (2013.01); *A61L 26/0066* (2013.01); *A61L 2300/10* (2013.01); *A61L 2300/21* (2013.01); *A61L 2300/41* (2013.01); *A61L 2300/412* (2013.01)

(58) Field of Classification Search
None
See application file for complete search history.

(56) References Cited

U.S. PATENT DOCUMENTS

| | | |
|---|---|---|
| 2003/0225356 A1 | 12/2003 | Kulichikhin et al. |
| 2010/0074963 A1 | 3/2010 | Bettle |
| 2016/0243159 A1 | 8/2016 | De Rijk |
| 2018/0042980 A1 | 2/2018 | Datt et al. |

FOREIGN PATENT DOCUMENTS

| | | |
|---|---|---|
| CN | 1656044 A | 8/2005 |
| CN | 101279737 A | 10/2008 |
| CN | 108144107 A | 6/2018 |
| CN | 109529023 A | 3/2019 |
| CN | 115581797 A | 1/2023 |
| EP | 1952804 A1 | 8/2008 |
| WO | 2012032364 A1 | 3/2012 |
| WO | 2019179611 A1 | 9/2019 |

OTHER PUBLICATIONS

Shahid et al "Antibacterial wound dressing eletrospun nanofibrous material from polyvinyl alcohol, honey and curcumin longa extract", Industrial Textiles, vol. 51(3)455-469 (Year: 2021).*
International Search Report dated Dec. 30, 2023 in International Application No. PCT/CN2023/120061. English translation attached.
The First Office Action from corresponding Chinese Application No. 202211237037.7, dated Mar. 4, 2023. English translation attached.
The Grant Notice from corresponding Chinese Application No. 202211237037.7, dated Apr. 23, 2023. English translation attached.
Sandrine Quignard et al. "Silica nanoparticles as sources of silicic acid favoring wound healing in vitro." Colloids and Surfaces B: Biointerfaces 155(2017):530-537.

* cited by examiner

*Primary Examiner* — Isis A Ghali

(57) ABSTRACT

The present disclosure specifically relates to a liquid dressing for promoting wound healing. The liquid dressing comprises components of, in percentage by weight: 1% to 2% of monomeric silicic acid and 98% to 99% of distilled water. The liquid dressing also comprises aloe, vitamin C, fish oil, and curcumin. The components comprise, in percentage by weight: 1% to 2% of monomeric silicic acid, 3% to 5% of aloe, 5% to 7% of vitamin C, 1% to 3% of fish oil, 1% to 2% of curcumin, and the balance being the distilled water. The liquid dressing for promoting wound healing in the present disclosure has a great promotion effect on wound healing, particularly in accelerating healing of refractory wounds caused by hyperglycemia. Moreover, the liquid dressing for promoting wound healing in the present disclosure has a certain auxiliary effect on other refractory wounds that do not heal for a long time.

3 Claims, No Drawings

LIQUID DRESSING FOR PROMOTING WOUND HEALING

FIELD

The present disclosure relates to the technical field of liquid dressing, and more particularly, to a liquid dressing for promoting wound healing.

BACKGROUND

Liquid dressing is a kind of liquid having a disinfection effect that can directly act on pathogens and have an inhibitory effect on most of bacteria, viruses and protozoa, including *Staphylococcus aureus, Escherichia coli, Hemolytic streptococcus*, and the like. The liquid, when sprayed on the wound, forms a layer of protective film to protect a wound, isolate the wound from an external environment, avoid the invasion of foreign pathogens and have a killing effect on the pathogens around the wound. When administered to the abdominal and perineal wounds, the liquid dressing has the effects of promoting wound healing and preventing infection. The liquid dressing is a product that can be used for disinfection and wound care. After the liquid dressing is used to cover the wound, it can not only kill the pathogens around the wound, but also play a role in protecting the wound. With the deep research and understanding of wounds, it has been discovered that if the wound can be kept in a moist and highly permeable environment, the wound would be maintained in a moist environment, which can accelerate the speed of wound healing. Therefore, compared with traditional wound care methods, the liquid dressing not only can promote healing in a moist environment, but can also eliminate bacteria and fungi in the healing environment, maintaining an optimal environment for wound healing.

Although the liquid dressings in the prior art can assist wound healing, the healing speed is slower. Moreover, most of the liquid dressings in the prior art have the function of promoting healing for newly formed wounds, and exhibits a poor promotion effect on chronic refractory wounds.

SUMMARY

In order to solve the above problems existing in the related art, the present disclosure provides a liquid dressing for promoting wound healing which has a great promotion effect on wound healing, and has an outstanding effect on accelerating healing of refractory wounds caused by hyperglycemia. Moreover, the liquid dressing has a certain auxiliary effect on other refractory wounds that do not heal for a long time.

Technical problems to be solved by the present disclosure are realized through the following technical solutions.

Provided is a liquid dressing for promoting wound healing, including the following components in percentage by weight: 1% to 2% of monomeric silicic acid and 98% to 99% of distilled water.

Further, the monomeric silicic acid is $Si(OH)_4$ or $H_2SiO_4$.

Further, the liquid dressing for promoting wound healing further includes: aloe, vitamin C, fish oil, and curcumin. The liquid dressing includes the following components in percentage by weight: 1% to 2% of monomeric silicic acid, 3% to 5% of aloe, 5% to 7% of vitamin C, 1% to 3% of fish oil, 1% to 2% of curcumin, and the balance being distilled water.

Further, the liquid dressing for promoting wound healing includes the following components in percentage by weight: 2% of monomeric silicic acid, 3% of aloe, 5% of vitamin C, 1% of fish oil, 1% of curcumin, and the balance being distilled water.

Provided is a method for preparing the liquid dressing for promoting wound healing. The method includes the following steps: step 1 of sequentially adding the monomeric silicic acid and the distilled water into a reaction kettle according to the composition ratio, and controlling a temperature to a range from 120 to 150° C.; step 2 of performing a stir in the reaction kettle, and keeping the temperature at 100° C. for 1 to 3 hours after the substances in the reaction kettle are completely dissolved; step 3 of lowering an internal temperature of the reaction kettle to 50° C., and leaving the mixed liquid after being uniformly mixed to stand; and step 4 of cooling the mixture obtained in step 3 to room temperature, and filling to obtain the liquid dressing.

Provided is a method for preparing the liquid dressing for promoting wound healing. The method includes the following steps: step 1 of sequentially adding the monomeric silicic acid, aloe, vitamin C, fish oil, curcumin, and distilled water into a reaction kettle according to the composition ratio, and controlling a temperature to a range from 120 to 150° C.; step 2 of performing a stir in the reaction kettle, and keeping the temperature at 100° C. for 1 to 3 hours after the substances in the reaction kettle are completely dissolved; step 3 of lowering an internal temperature of the reaction kettle to 50° C., and leaving the mixed liquid after being uniformly mixed to stand; and step 4 of cooling the mixture obtained in step 3 to room temperature, and filling to obtain the liquid dressing.

Provided is a method for promoting wound healing. The method includes: applying the liquid dressing for promoting wound healing as described above to a wound.

Further, the frequency of application is three times a day.

Compared with the prior art, the present disclosure has the following beneficial effects.

Firstly, the liquid dressing for promoting wound healing in the present disclosure has a great promotion effect on wound healing, particularly in accelerating the healing of refractory wounds caused by hyperglycemia. Moreover, the liquid dressing for promoting wound healing in the present disclosure has a certain auxiliary effect on other refractory wounds that do not heal for a long time.

Secondly, with the liquid dressing for promoting wound healing in the present disclosure, the liquid dressing is prepared by adding monomeric silicic acid, aloe, vitamin C, and fish oil. In this way, a healing function of the wound is promoted. Moreover, an anti-inflammatory function can be remarkably improved by the addition of curcumin.

DETAILED DESCRIPTION

The present disclosure will be further described in detail below with reference to specific embodiments, but implementations of the present disclosure are not limited thereto.

Example 1

The example provides a liquid dressing for promoting wound healing. The liquid dressing includes components: 2% of monomeric silicic acid and 98% of distilled water in percentage by weight. The monomeric silicic acid in the present example is $Si(OH)_4$.

Provided is a method for preparing the liquid dressing in the present example, which includes the following steps: step 1 of sequentially adding 2% of the monomeric silicic acid $(Si(OH)_4)$ and 98% of the distilled water into a reaction kettle, and controlling a temperature to a range from 120° C. to 150° C.; step 2 of performing a stir in the reaction kettle, and keeping the temperature at 100° C. for 3 hours after the substances in the reaction kettle are completely dissolved; step 3 of lowering an internal temperature of the reaction kettle to 50° C., and leaving the mixed liquid after being uniformly mixed to stand; and step 4 of cooling the mixture obtained in step 3 to room temperature, and filling to obtain the liquid dressing.

Example 2

The example provides a liquid dressing for promoting wound healing. The liquid dressing includes the following components: 2% of monomeric silicic acid and 98% of distilled water in percentage by weight. The monomeric silicic acid in the present example is $H_2SiO_4$.

Provided is a method for preparing the liquid dressing in the present example, which includes the following steps: step 1 of sequentially adding 2% of the monomeric silicic acid ($H_2SiO_4$) and 98% of the distilled water into a reaction kettle, and controlling a temperature to a range from 120° C. to 150° C.; step 2 of performing a stir in the reaction kettle, and keeping the temperature at 100° C. for 3 hours after the substances in the reaction kettle are completely dissolved; step 3 of lowering an internal temperature of the reaction kettle to 50° C., and leaving the mixed liquid after being uniformly mixed to stand; and step 4 of cooling the mixture obtained in step 3 to room temperature, and filling to obtain the liquid dressing.

Example 3

The example provides a liquid dressing for promoting wound healing. The liquid dressing includes the following components: 1% of monomeric silicic acid and 99% of distilled water in percentage by weight. The monomeric silicic acid in the present example is $Si(OH)_4$.

Provided is a method for preparing the liquid dressing in the present example, which includes the following steps: step 1 of sequentially adding 1% of the monomeric silicic acid ($Si(OH)_4$) and 99% of the distilled water into a reaction kettle, and controlling a temperature to a range from 120° C. to 150° C.; step 2 of performing a stir in the reaction kettle, and keeping the temperature at 100° C. for 2 hours after the substances in the reaction kettle are completely dissolved; step 3 of lowering an internal temperature of the reaction kettle to 50° C., and leaving the mixed liquid after being uniformly mixed to stand; and step 4 of cooling the mixture obtained in step 3 to room temperature, and filling to obtain the liquid dressing.

Example 4

The example provides a liquid dressing for promoting wound healing. The liquid dressing includes the following components: 1% of monomeric silicic acid and 99% of distilled water in percentage by weight. The monomeric silicic acid in the present example is $H_2SiO_4$.

Provided is a method for preparing the liquid dressing in the present example, which includes the following steps: step 1 of sequentially adding 1% of the monomeric silicic acid ($H_2SiO_4$) and 99% of the distilled water into a reaction kettle, and controlling a temperature to a range from 120° C. to 150° C.; step 2 of performing a stir in the reaction kettle, and keeping the temperature at 100° C. for 2 hours after the substances in the reaction kettle are completely dissolved; step 3 of lowering an internal temperature of the reaction kettle to 50° C., and leaving the mixed liquid after being uniformly mixed to stand; and step 4 of cooling the mixture obtained in step 3 to room temperature, and filling to obtain the liquid dressing.

Example 5

The example provides a liquid dressing for promoting wound healing. The liquid dressing includes the following components in percentage by weight: 2% of monomeric silicic acid, 3% of aloe, 5% of vitamin C, 1% of fish oil, 1% of curcumin, and the balance is distilled water. The monomeric silicic acid in the present example is $Si(OH)_4$.

Provided is a method for preparing the liquid dressing in the present example, which includes the following steps: step 1 of sequentially adding the monomeric silicic acid, aloe, vitamin C, fish oil, curcumin, and distilled water into a reaction kettle according to the composition ratio, and controlling a temperature to a range from 120° C. to 150° C.; step 2 of performing a stir in the reaction kettle, and keeping the temperature at 100° C. for 3 hours after the substances in the reaction kettle are completely dissolved; step 3 of lowering an internal temperature of the reaction kettle to 50° C., and leaving the mixed liquid after being uniformly mixed to stand; and step 4 of cooling the mixture obtained in step 3 to room temperature, and filling to obtain the liquid dressing.

Example 6

The present example provides a liquid dressing for promoting wound healing. The liquid dressing includes the following components in percentage by weight: 2% of monomeric silicic acid, 5% of aloe, 7% of vitamin C, 3% of fish oil, 1% of curcumin, and the balance is distilled water. The monomeric silicic acid in the present example is $H_2SiO_4$.

Provided is a method for preparing the liquid dressing in the present example, which includes the following steps: step 1 of sequentially adding the monomeric silicic acid, aloe, vitamin C, fish oil, curcumin, and distilled water into a reaction kettle according to the composition ratio, and controlling a temperature to a range from 120° C. to 150° C.; step 2 of performing a stir in the reaction kettle, and keeping the temperature at 100° C. for 1 hour after the substances in the reaction kettle are completely dissolved; step 3 of lowering an internal temperature of the reaction kettle to 50° C., and leaving the mixed liquid after being uniformly mixed to stand; and step 4 of cooling the mixture obtained in step 3 to room temperature, and filling to obtain the liquid dressing.

Example 7

The present example provides a liquid dressing for promoting wound healing. The liquid dressing includes the following components in percentage by weight: 1% of monomeric silicic acid, 4% of aloe, 6% of vitamin C, 2% of fish oil, 2% of curcumin, and the balance is distilled water. The monomeric silicic acid in the present example is $H_2SiO_4$.

Provided is a method for preparing the liquid dressing in the present example, which includes the following steps: step 1 of sequentially adding the monomeric silicic acid, aloe, vitamin C, fish oil, curcumin, and distilled water into a reaction kettle according to the composition ratio, and controlling a temperature to a range from 120° C. to 150° C.; step 2 of performing a stir in the reaction kettle, and keeping the temperature at 100° C. for 2 hours after the substances in the reaction kettle are completely dissolved; step 3 of lowering an internal temperature of the reaction kettle to 50° C., and leaving the mixed liquid after being uniformly mixed to stand; and step 4 of cooling the mixture obtained in step 3 to room temperature, and filling to obtain the liquid dressing.

The finished liquid dressing is prepared by using the above-mentioned examples. The liquid dressing prepared according to the present disclosure is applied to wounds of individuals with different types of wounds. The prepared liquid dressing is dripped onto the wound, and applied gently and uniformly to cover the wound completely. The frequency of application is three times a day: in the morning, afternoon, and evening. Following the application, observations were made and the results are shown as follows:

|  | Time to effect and Symptoms Example 1 | Time to effect and Symptoms Example 2 | Time to effect and Symptoms Example 5 | Time to effect and Symptoms Example 6 |
| --- | --- | --- | --- | --- |
| Patients with common wounds | Taking effect on the same day and alleviating wound pains | Taking effect on the same day and alleviating the wound pains | Taking effect on the next day, taking effect within 3 days for the refractory wounds, and gradually healing the wounds | Taking effect on the same day and alleviating the wound pains |
| Patients with hyperglycemia | Taking effect on the next day, taking effect within 3 days for the refractory wounds, and gradually healing the wounds | Taking effect on the next day, taking effect within 3 days for the refractory wounds, and accelerating the wound healing speed | Taking effect on the next day, taking effect within 3 days for the refractory wounds, and gradually healing the wounds | Relieving pains within half a minute, accelerating the wound healing speed, and taking effect on the same day |
| Patients with scalds | Relieving pains within half a minute, accelerating the wound healing speed, and taking effect on the same day | Relieving pains within a minute, accelerating the wound healing speed, and taking effect on the same day | Taking effect on the next day, accelerating the wound healing speed, and taking effect on the same day | Relieving pains within half a minute, taking effect within 3 days for the refractory wounds, and gradually healing the wounds |

Based on the reactions and time to effect after the liquid dressing prepared according to the present disclosure is used by patients with different kinds of wounds in the above table, it can be concluded that the liquid dressing prepared according to the present disclosure can accelerate the wound healing speed. Moreover, the liquid dressing can take effect within three days for the refractory wounds, resulting in gradually healing the wounds. Therefore, it is evident that the present disclosure can expedite the wound healing speed and assist in the healing of the wounds that do not heal for a long time.

The above content is a further detailed description of the present disclosure in combination with specific preferred embodiments. Moreover, it cannot be affirmed that the specific embodiments of the present disclosure is limited to these descriptions. For a person of ordinary skill in the art to which the present disclosure belongs, several simple deductions or replacements may also be made without departing from the concept of the present disclosure, and should all be considered to be within the scope of the present disclosure.

What is claimed is:

1. A liquid dressing for promoting wound healing, consisting of, in percentage by weight:

1% to 2% of monomeric silicic acid and 98% to 99% of distilled water;

wherein the monomeric silicic acid is Si(OH)$_4$;

wherein the liquid dressing for promoting wound healing is prepared by a method comprising the following steps:

step 1 of sequentially adding the monomeric silicic acid and the distilled water into a reaction kettle according to the composition ratio, and controlling a temperature to a range from 120° C. to 150° C.;

step 2 of performing a stir in the reaction kettle, and keeping the temperature at 100° C. for 1 to 3 hours after the substances in the reaction kettle are completely dissolved;

step 3 of lowering an internal temperature of the reaction kettle to 50° C., and leaving the mixed liquid after being uniformly mixed to stand; and step 4 of cooling the mixture obtained in the step 3 to room temperature to obtain the liquid dressing.

2. A liquid dressing for promoting wound healing, consisting of:

in percentage by weight: 1% to 2% of monomeric silicic acid, 3% to 5% of aloe, 5% to 7% of vitamin C, 1% to 3% of fish oil, 1% to 2% of curcumin, and the balance being the distilled water;

wherein the liquid dressing for promoting wound healing is prepared by a method comprising the following steps:

step 1 of sequentially adding the monomeric silicic acid, aloe, vitamin C, fish oil, curcumin, and distilled water into a reaction kettle according to the composition ratio, and controlling a temperature to a range from 120° C. to 150° C.;

step 2 of performing a stir in the reaction kettle, and keeping the temperature at 100° C. for 1 to 3 hours after the substances in the reaction kettle are completely dissolved;

step 3 of lowering an internal temperature of the reaction kettle to 50° C., and leaving the mixed liquid after being uniformly mixed to stand; and step 4 of cooling the mixture obtained in step 3 to room temperature to obtain the liquid dressing.

3. The liquid dressing for promoting wound healing according to claim 2, consisting of, in percentage by weight:

2% of monomeric silicic acid, 3% of aloe, 5% of vitamin C, 1% of fish oil, 1% of curcumin, and the balance being the distilled water.

* * * * *